United States Patent [19]

Rothgery

[11] 4,282,371

[45] Aug. 4, 1981

[54] SELECTED AMINOESTER DERIVATIVES OF TRICHLOROACETONITRILE

[75] Inventor: Eugene F. Rothgery, North Branford, Conn.

[73] Assignee: Olin Corporation, New Haven, Conn.

[21] Appl. No.: 144,744

[22] Filed: Apr. 28, 1980

[51] Int. Cl.$^3$ .................... C07C 101/24; A01N 37/50
[52] U.S. Cl. ......................... 560/35; 560/22; 560/156; 560/168; 424/309; 424/311; 71/106; 71/108; 71/111
[58] Field of Search ............... 560/35, 168, 22, 156

[56] References Cited

U.S. PATENT DOCUMENTS

| | | | |
|---|---|---|---|
| 3,663,606 | 5/1972 | Isowa | 560/168 |
| 3,890,339 | 6/1975 | Gavin | 548/129 |

OTHER PUBLICATIONS

Saari, Chem. Absts., 85, 123391(r), (1976).
Ried et al., Chem. Ber., 95, 728, (1961).
Cramer et al., Chem. Ber., 91, 1049, (1958).
Grivas et al., Can. J. Chem., 36, (1958).

Primary Examiner—G. T. Breitenstein
Attorney, Agent, or Firm—William A. Simons; Thomas P. O'Day

[57] ABSTRACT

Disclosed are selected aminoester derivatives of the formula:

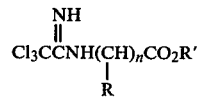

wherein R is hydrogen, lower alkyl having 1 to 4 carbon atoms, phenyl, benzyl, and substituted phenyl and benzyl in which said phenyl ring substituents are selected from lower alkyl having 1 to 4 carbon atoms, lower alkoxy having 1 to 4 carbon atoms, halo, hydroxy, nitro, amino and mixtures thereof; wherein R' is lower alkyl having 1 to 4 carbon atoms; and n is 1 or 2. Examples of these compounds have shown bactericidal and herbicidal activity.

8 Claims, No Drawings

SELECTED AMINOESTER DERIVATIVES OF TRICHLOROACETONITRILE

BACKGROUND OF THE INVENTION

1. Field of the Invention

The present invention relates to selected aminoester derivatives of trichloroacetonitrile.

2. Description of the Prior Art

Trichloroacetonitrile is a known intermediate for several compounds having pesticidal activity, including 3-trichloromethyl-5-ethoxy-1,2,4-thiadiazole. See U.S. Pat. No. 3,890,339, which issued to D. Gavin on June 17, 1975.

Furthermore, amidines resulting from the reaction of alkylamines with trichloroacetonitrile are known as heart stimulants. See *Chemical Abstracts*, 85, 123391r.

BRIEF SUMMARY OF THE INVENTION

Accordingly, the present invention is directed to, as compositions of matter, selected aminoester derivatives of trichloroacetonitrile of the formula:

$$Cl_3CCNH(CH)_nCO_2R' \quad \text{(I)}$$
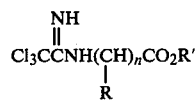

wherein R is hydrogen, lower alkyl having 1 to 4 carbon atoms, phenyl, benzyl and substituted phenyl and benzyl in which said phenyl ring substituents are selected from lower alkyl having 1 to 4 carbon atoms, lower alkoxy having 1 to 4 carbon atons, halo (e.g., fluoro, chloro, and bromo), hydroxy, nitro, amino and mixtures thereof; wherein R' is lower alkyl having 1 to 4 carbon atoms; and n is 1 or 2.

DETAILED DESCRIPTION

The aminoester derivatives of the present invention may be prepared by reacting the corresponding free aminoester with either trichloroacetonitrile or its methyl ester, methyl trichloroacetimidate. These general reactions are illustrated below in equations (A) and (B). In equation (A), trichloroacetonitrile is reacted with ethyl glycinate to produce ethyl (N-trichloroacetamido)glyinate. In equation (B), methyl trichloroacetimidate is reacted with ethyl β-alanate to produce ethyl(N-trichloroacetimidoyl)-β-alanate and methanol.

$$Cl_3CCN + H_2NCH_2CO_2C_2H_5 \longrightarrow \quad \text{(A)}$$
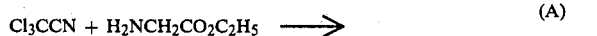
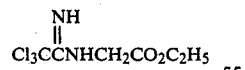
$$Cl_3CCOCH_3 + H_2N(CH_2)_2CO_2C_2H_5 \longrightarrow \quad \text{(B)}$$
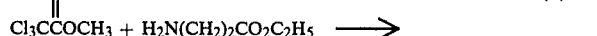
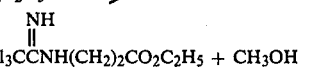

Trichloroacetonitrile (TCAN) is a commercially available compound and its above-mentioned methyl ester may be easily prepared by reaction of TCAN with methanol in the presence of a base. See an article by F. Cramer et al, *Chem. Ber.*, 91, page 1049 (1958) as an example of such a synthesis.

Examples of suitable aminoester reactants may be made from the corresponding hydrochloride salts. Preferably, the free aminoesters may be obtained from the hydrochloride salts by neutralization with ammonia. Generally, these hydrochloride salts of the aminoester reactants can be obtained from corresponding amino acids using conventional esterification techniques in alcohol saturated with HCl.

Representative aminoester reactants of the present invention include the following (where R' is as defined above):

Beta Alanine Esters - $H_2N-(CH_2)_2-CO_2R'$

Alanine Esters - 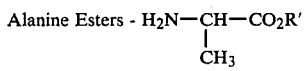

Glycine Esters - $H_2N-CH_2CO_2R'$

Leucine Esters - 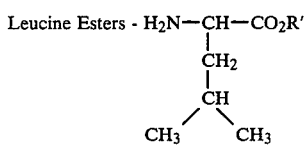

Norleucine Esters - $H_2N-CH-CO_2R'$

Phenylglycine Esters - $H_2N-CH-CO_2R'$

Tyrosine Esters - 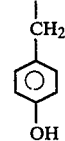

Valine Esters - 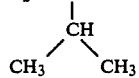

It should be noted that the present invention contemplates the use of either the L form, D form or DL form of aminoester reactants.

Suitable conventional reaction conditions may be employed in the synthesis of the present compounds and the present invention is not intended to be limited to any particular reaction conditions. Advantageously, and preferably, the reaction is carried out with an equimolar ratio of trichloroacetonitrile or methyl trichloroacetimidate to the selected aminoester, or a slight molar excess of the former (e.g., from about 1:1 to 1.5:1). A solvent is not necessary, but any suitable inert solvent may be employed. The reaction temperature and time will both depend upon the exact reactants being employed, but in most situations, reaction temperatures from about 5° C. to about 100° C. and reaction times from about 1 hour to about 12 hours are preferred. The desired product may be recovered from the reaction mixture by any conventional means, for example, filtration, extraction and the like. Finally, it should be noted that while the reactions illustrated by Equations (A) and (B) are preferred methods for preparing compounds of the present invention, other synthesis methods may also be employed.

Compounds of the present invention have shown utility as active pesticides, including bactericides and herbicides. For example, ethyl (N-trichloroacetimidoyl) glycinate has shown activity against *Pseudomonas phaseoli* and *Xanthomonas phaseoli*, even when this chemical was used in a concentration of 33 parts per million (ppm) by weight. This compound showed good activity as a pre-herbicide against foxtail millet, Japanese millet, morning glory and crabgrass at an applied amount of 10 pounds per acre. Ethyl (N-trichloroacetimidoyl)-β-alanate also showed good activity as a pre-herbicide against foxtail millet, Japanese millet, crabgrass, pigweed, and sesbania at the application level of 10 pounds per acre. Methyl (N-trichloroacetimidoyl)-DL-alanate showed some activity as a soil fungicide against *pythium* and *T. basicola*. Methyl (N-trichloroacetimidoyl-L-tyrosinate also showed good activity as a pre-herbicide.

The following examples further illustrate the present invention. All parts and percentages employed therein are by weight unless otherwise indicated.

EXAMPLE 1

Ethyl (N-Trichloroacetimidoyl)glycinate

Into an ethyl ether slurry of ethyl glycinate hydrochloride (14 g, 0.1 mole) was bubbled ammonia gas. The resultant ammonium chloride was filtered off and the solvent removed. The free aminoester was immediately poured into trichloroacetonitrile (15 g, 0.11 mole) at 5° C. in an ice bath. After exotherming to 18° C. the mixture was stirred for about 16 hours at ambient temperature. Cooling gave a yellow solid, which was recrystallized from ethyl ether/ligroin to give 6.6 g (about 28% yield) of material of m.p. 25°–27° C.

Calculated for $C_6H_9Cl_3N_2$: C, 29.12; H, 3.67; Cl, 42.97; N, 11.32; Found: C, 29.16; H, 3.55; Cl, 43.12; N, 11.45.

EXAMPLE 2

Ethyl (N-Trichloroacetimidoyl)-β-Alanate

Ethyl β-alanate hydrochloride (7.7 g, 0.06 mole) was slurried in 200 ml of ethyl ether and 30 ml of ammonia slowly added. The resulting ammonium chloride was filtered off and the solvent removed to give 5.2 g of an oil. This was mixed with methyl trichloroacetimidate and stirred for about 16 hours. The reaction mixture was extracted with petroleum ether. Cooling gave 2 g (13% yield) of the product as an oil.

Calculated for $C_7H_{11}Cl_3N_2O_2$: C, 32.14; H, 4.24; Cl, 40.67; N, 10.71; Found: C, 31.96; H, 4.04; Cl, 40.74; N, 10.48

EXAMPLE 3

Methyl (N-Trichloroacetimidoyl)-DL-Alanate

Methyl DL-alanate hydrochloride (7.7 g, 0.05 mole) was slurried in 200 ml of ether and 30 ml of ammonia added slowly. After 20 minutes the solids were filtered off and the solvent removed to give a 3 g of liquid. This was added to methyl trichloroacetamidate (7 g, 0.05 mole) and the mixture stirred for about 16 hours at ambient temperature. The reaction mixture was extracted with hot petroleum ether. On cooling the solution gave 0.9 g (8% yield) of an oily product.

Calculated for $C_6H_9Cl_3N_2O_2$: C, 29.11; H, 3.67; Cl, 42.97; N, 11.32; Found: C, 29.05; H, 3.49; Cl, 42.73; N, 11.33

EXAMPLE 4

Methyl (N-Trichloroacetimidoyl)-L-tyrosinate

Methyl L-tyrosinate (3 g) was added to excess methyl trichloroacetimadate and heated to a slight reflux for five minutes. A solid by-product was filtered off and the filtrate partially evaporated to give 3.9 g (75% yield) of product. mp 96° C. (decomposed). The product was characterized by IR and elemental analyses.

Calculated for $C_{12}H_{13}Cl_3N_2O_3$: C, 42.44; H, 3.86; Cl, 31.32; N, 8.25; Found: C, 42.23; H, 3.76; Cl, 31.37; N, 8.23

What is claimed is:

1. A compound of the formula:

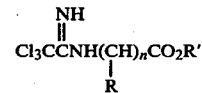

wherein R is hydrogen, lower alkyl having 1 to 4 carbon atoms, phenyl, benzyl, and substituted phenyl and benzyl in which said phenyl ring substituents are selected from the group consisting of lower alkyl having 1 to 4 carbon atoms, lower alkoxy having 1 to 4 carbon atoms, halo, hydroxy, nitro, amino and mixtures thereof; wherein R' is a lower alkyl having 1 to 4 carbon atoms and n is 1 or 2.

2. The compound of claim 1 wherein n=1.

3. The compound of claim 2 wherein R is hydrogen or a lower alkyl having 1 to 4 carbon atoms.

4. The compound of claim 3 being ethyl (N-trichloroacetimidoyl)glycinate.

5. The compound of claim 3 being methyl (N-trichloroacetimidoyl)alanate.

6. The compound of claim 2 being methyl (N-trichloroacetimidoyl)tyrosinate.

7. The compound of claim 1 wherein n=2.

8. The compound of claim 1 being ethyl (N-trichloroacetimidoyl)-beta-alanate.

* * * * *